US012640268B2

(12) United States Patent
Chen et al.

(10) Patent No.: US 12,640,268 B2
(45) Date of Patent: May 26, 2026

(54) AUXILIARY ASSESSMENT METHOD AND SYSTEM FOR CARDIAC FUNCTION

(71) Applicant: KAOHSIUNG MEDICAL UNIVERSITY, Kaohsiung (TW)

(72) Inventors: Chao-Wen Chen, Kaohsiung City (TW); Hao-Yun Kao, Kaohsiung City (TW); Yu-Cheng Chuang, Kaohsiung City (TW); Jo-Nan Wu, Kaohsiung City (TW); Wen-Yen Chang, Kaohsiung City (TW)

(73) Assignee: KAOHSIUNG MEDICAL UNIVERSITY, Kaohsiung City (TW)

( * ) Notice: Subject to any disclaimer, the term of this patent is extended or adjusted under 35 U.S.C. 154(b) by 407 days.

(21) Appl. No.: 18/225,702

(22) Filed: Jul. 25, 2023

(65) Prior Publication Data

US 2024/0194338 A1 Jun. 13, 2024

(30) Foreign Application Priority Data

Dec. 8, 2022 (TW) .................................. 111147244

(51) Int. Cl.
 *G16H 50/20* (2018.01)
 *A61B 5/0255* (2006.01)
(52) U.S. Cl.
 CPC ........... *G16H 50/20* (2018.01); *A61B 5/0255* (2013.01)

(58) Field of Classification Search
 CPC ..... G16H 50/20; A61B 5/0255; A61B 5/1112; A61B 5/1118; A61B 5/222; A61B 5/329; A61B 5/02438
 See application file for complete search history.

(56) References Cited

U.S. PATENT DOCUMENTS

2017/0258367 A1 9/2017 Cheng
2018/0325385 A1* 11/2018 Deterding .............. G16H 50/20

OTHER PUBLICATIONS

RunningAhead ( "Heart beats per kilometer" Aug. 25, 2011)(https://www.runningahead.com/forums/topic/f263286cf2a74648bb9c769600cd370b)("NPL1") (Year: 2011).*

* cited by examiner

*Primary Examiner* — Tse W Chen
*Assistant Examiner* — Joseph A Tombers
(74) *Attorney, Agent, or Firm* — WPAT, PC

(57) ABSTRACT

An auxiliary assessment method for cardiac function performed by a computing unit includes collecting a number of heartbeats and an amount of movement of a subject in a period of time; and calculating a distance per beat to assess cardiac function of the subject. The distance per beat is defined by dividing the amount of movement by the number of heartbeats. A length of the period of time is defined between at least two adjacent heartbeats. The amount of movement corresponds to a cumulative amount of movement in the period of time.

14 Claims, 2 Drawing Sheets

AUXILIARY ASSESSMENT METHOD AND SYSTEM FOR CARDIAC FUNCTION

CROSS REFERENCE TO RELATED APPLICATION

The application claims the benefit of Taiwan application serial No. 111147244, filed on Dec. 8, 2022, and the entire contents of which are incorporated herein by reference.

BACKGROUND OF THE INVENTION

1. Field of the Invention

The present invention relates to an assessment method and system and, more particularly, to an auxiliary assessment method and system for cardiac function.

2. Description of the Related Art

The heart rate, respiration rate, blood pressure, etc. of a subject/user can be obtained independently by conventional cardiac function assessment/monitoring methods. However, the subject cannot clearly know the current state and ability of his/her heart function from these data respectively. Therefore, the subject/user cannot assess whether his/her heart can afford the load during the current/subsequent exercise. Exercising without knowing the current condition of the heart may increase the incidence of injuries or accidents, especially sudden cardiac death.

In light of the above, it is necessary to improve the conventional cardiac function assessment methods.

SUMMARY OF THE INVENTION

In order to resolve the above problem, it is an objective of the present invention to provide an auxiliary assessment method for cardiac function, which is capable of assessing cardiac function.

It is another objective of the present invention to provide an auxiliary assessment system for cardiac function, which is capable of performing the auxiliary assessment method for cardiac function.

As used herein, the term "a", "an" or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

As used herein, the term "coupling" includes direct or indirect electric and/or signal connection, which can be selected by one of ordinary skill in the art according to use requirements.

As used herein, the term "computing unit" refers to any data processing device that has specific functions and that is implemented by hardware or hardware and software, in particular a processor or a computer with a processor to process analysis information and/or generate corresponding control information, such as an electronic controller, a server, a cloud platform, a virtual machine, a desktop computer, a notebook computer, a tablet computer, or a smartphone, which may be understood by one of ordinary skill in the art of the present invention. In addition, a corresponding data receiving or transmission unit may be included to receive or transmit required data. Moreover, a corresponding database or data storage unit may be included to store required data. In particular, unless otherwise specifically excluded or contradicted, the "computing unit" may be a "combination of multiple computing units" based on a distributed system architecture, and is configured to include or represent a process, mechanism, and result of information stream processing among multiple computing units.

The present invention provides an auxiliary assessment method for cardiac function, performing following steps by a computer: collecting a number of heartbeats and an amount of movement of a subject in a period of time; and calculating a distance per beat to assess cardiac function of the subject. The distance per beat is defined by dividing the amount of movement by the number of heartbeats. A length of the period of time is defined between at least two adjacent heartbeats, and the amount of movement corresponds to a cumulative amount of movement in the period of time.

The present invention provides an auxiliary assessment system for cardiac function, including a heart rate detection unit, a distance detection unit, and a computing unit. The heart rate detection unit is configured to measure a number of heartbeats of a subject in a period of time. The distance detection unit is configured to measure an amount of movement of the subject in the period of time. The computing unit is coupled to the heart rate detection unit and the distance detection unit, and is configured to receive the number of heartbeats and the amount of movement and perform the auxiliary assessment method for cardiac function.

Based on this, by the auxiliary assessment method and system for cardiac function of the present invention, the defined distance per beat can be calculated based on the easy-to-measure physical quantities (an amount of movement and a number of heartbeats). The distance per beat is a physiological mechanism based on an activity volume and a number of heartbeats corresponding to cardiac blood output, and has statistical significance in the corresponding research, which is adapted to assessment of cardiac function, especially can achieve the effect of auxiliary assessment of heart health. The corresponding distance per beat is generated by the corresponding system, to facilitate implementation and application of the assessment method.

In an example, the number of heartbeats and the amount of movement are collected by the subject under a specific condition, and the specific condition includes the number of heartbeats and the amount of movement obtained when the subject moves at different levels of intensity in a Borg rating of perceived exertion scale that ranges from 6 to 20 in the period of time. Thus, through the defined specific data collection, the subjective feelings in the Borg rating of perceived exertion scale correspond to the objective numerical values, which helps to improve the validity and reliability of the defined distance per beat for assessment of cardiac function.

In an example, in the process of calculating the distance per beat, a first threshold interval is pre-defined based on an effective statistical confidence interval, the first threshold interval includes a first upper limit and a first lower limit, and when the distance per beat is greater than the first upper limit or less than the first lower limit, a first warning signal is sent. Thus, through the defined first threshold interval, a warning signal may be sent when the distance per beat of the subject exceeds the first threshold interval, thereby warning the subject to pay attention to the current condition of cardiac function.

In an example, a normalized three-kilometer distance per beat is defined by multiplying the distance per beat by 3 and dividing the product by a speed of the subject in the period of time, the speed is measured in kilometers per hour and calculated by dividing the amount of movement by the period of time, a standard value and a tolerance are set, and when an absolute value of a difference between the normalized three-kilometer distance per beat and the standard value is greater than the tolerance, a warning signal is sent. Thus, through the defined normalized three-kilometer distance per beat and the corresponding tolerance, a warning signal may be sent when the absolute value of the difference between the normalized three-kilometer distance per beat of the subject and the standard value is greater than the tolerance, thereby warning the subject to pay attention to the current condition of cardiac function.

In an example, the standard value is 50, and optionally the range of tolerance is 5 to 30. In an example, for a person belonging class I of heart failure, the standard value is 40. In an example, for a person belonging class II of heart failure, the standard value is 33.4. In an example, for a person belonging class III of heart failure, the standard value is 23.8. Thus, through the given specific standard values of the distance per beat and corresponding optional tolerances, the cardiac function of the measured subject can be observed and/or evaluated. Preferably, when the difference between the measured value and the standard value is greater than the corresponding tolerance, a warning signal is generated thereby effectively warning the subject to pay attention to the current condition of cardiac function.

In an example, the distance per beat is positively correlated with a maximum oxygen consumption of the subject. Preferably, a ratio of an average value of the maximum oxygen consumption and an average value of the distance per beat ranges from 0.5 to 0.7. Thus, the distance per beat may be used as a reference for the maximum oxygen consumption to be used as a different reference indicator for assessment of cardiac function.

In an example, the distance per beat is positively correlated with an anaerobic threshold of the subject. Preferably, a ratio of an average value of the anaerobic threshold and an average value of the distance per beat ranges from 0.039 to 0.054. Thus, the distance per beat may be used as a reference for the anaerobic threshold to be used as a different reference indicator for assessment of cardiac function.

In an example, the distance per beat is positively correlated with an oxygen pulse of the subject. Preferably, a ratio of an average value of the oxygen pulse and an average value of the distance per beat ranges from 0.20 to 0.27. Thus, the distance per beat may be used as a reference for the oxygen pulse to be used as a different reference indicator for assessment of cardiac function.

In an example, the distance per beat is positively correlated with a cardio force index with peak acceleration. Preferably, a ratio of an average value of the distance per beat and an average value of the cardiac force index with peak acceleration is 6. Thus, the distance per beat may be used as a reference for the cardio force index with peak acceleration to be used as a different reference indicator for assessment of cardiac function.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
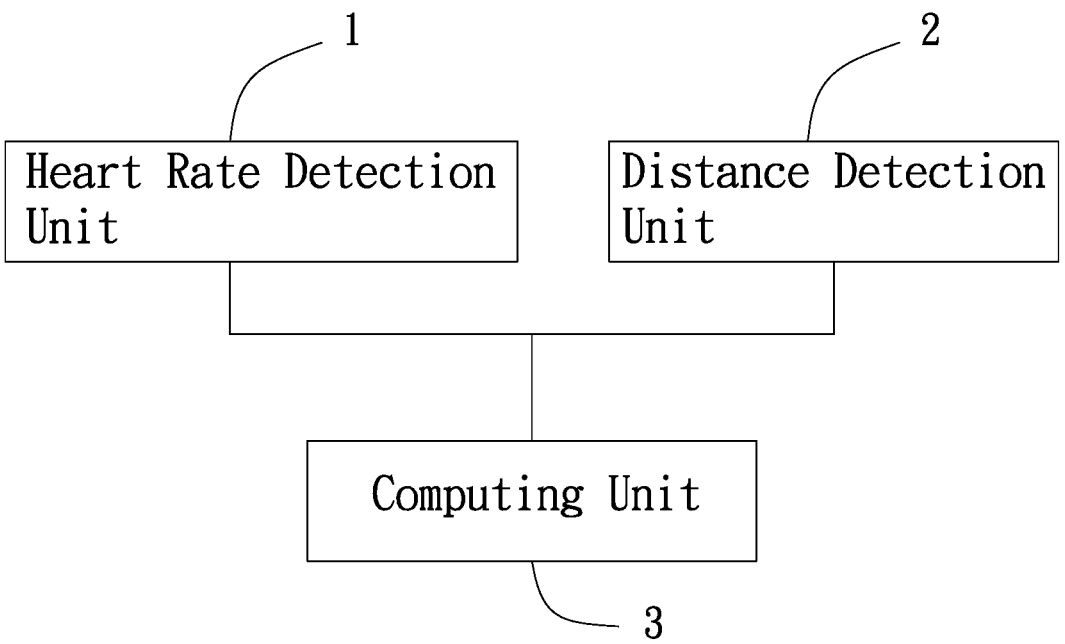
FIG. 1 is a schematic diagram of a system architecture according to a preferred embodiment of the present invention.

With reference to FIG. 1, which is a schematic diagram of a system architecture according to a preferred embodiment of the present invention, the system of the present invention includes a heart rate detection unit 1, a distance detection unit 2, and a computing unit 3. The computing unit 3 is coupled to the heart rate detection unit 1 and the distance detection unit 2, respectively, to calculate a distance per beat (DPB).

The heart rate detection unit 1 may be a contact or contactless heart rate monitoring device, preferably a wearable/contact device, that can move with the subject and detect a heart rate of a subject at any time and/or in real time. The heart rate refers to a number of heartbeats in a period of time.

The distance detection unit 2 is configured to detect an amount of movement of the subject in real time. The distance detection unit 2 may be, for example, a device with a global positioning system (GPS), an accelerometer, a gyroscope, and/or a device to which relevant positioning methods or distance measurements (such as triangulation) are applied. In addition, the distance detection unit 2 may be worn on the subject to detect the amount of movement of the subject at any time and/or in real time. Alternatively, the distance detection unit 2 may not be worn on the subject and, for example, may be a treadmill that can measure an amount of movement, or may be implemented by recording and identifying a movement distance through images. Taking a treadmill that can measure an amount of movement as an example, the corresponding amount of movement may be, for example, calculated based on a preset speed of the treadmill or a rotation distance or number of revolutions of the belt of the treadmill. However, the method for obtaining the amount of movement of the subject is not limited to the contents above. In particular, the amount of movement refers to a cumulative amount of movement in a period of time. For example, if a subject walks 100 meters from an origin to each of east, south, west, and north and back to the origin, the amount of movement is a sum of absolute values for every movement vector that the subject made, which is 400 meters in total. Any directional vectors, such as horizontal vector, vertical vector or inclined vector, could also be summed respectively. The amount of movement may be measured in kilometers, meters, centimeters, millimeters, miles, yards, feet, inches, etc., or may be measured in a custom unit according to a certain standard. The present invention is not limited in this regard. Preferably, the amount of movement is measured in centimeters, so that the distance per beat (DPB) is centimeters per beat (CMPB) measured in centimeters. Optionally, the distance per beat may be converted into a normalized value in a range of 0 to 1 or 0 to 100 or any interval under the same standard conditions.

The computing unit 3 is coupled to the heart rate detection unit 1 and the distance detection unit 2, to receive the heart rate detected by the heart rate detection unit 1 and the amount of movement detected by the distance detection unit 2, and calculate a distance per beat by dividing the amount of movement by the number of heartbeats.

Figure 2:
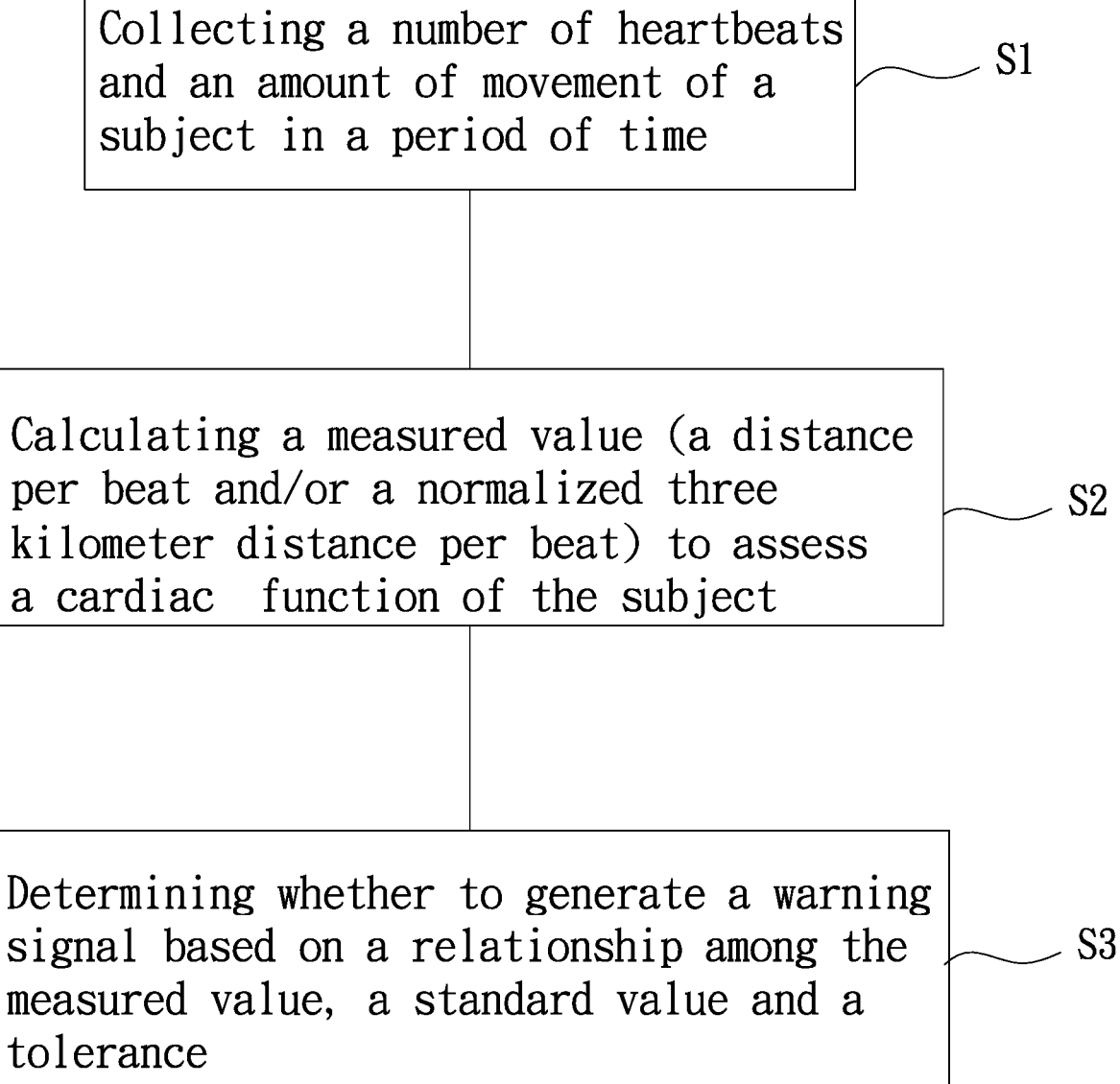
FIG. 2 is a schematic flowchart of a method according to a preferred embodiment of the present invention.

According to the above system, with reference to FIG. 2, an auxiliary assessment method for cardiac function may be implemented in the present invention by performing the following steps by a computing unit 3. Step S1 is to Collect a number of heartbeats and an amount of movement of a subject in a period of time. Step S2 is to Calculate a distance per beat to assess a cardiac function of the subject, where the distance per beat is defined by dividing the amount of movement by the number of heartbeats. A length of the period of time is not particularly limited, and is preferably defined between at least two adjacent heartbeats. The amount of movement refers to a cumulative amount of movement in a period of time. Preferably, the amount of movement is measured in centimeters.

Specifically, according to the research results and statistical results of the experiments corresponding to the present invention, the distance per beat may be data measured by the subject under any specific condition/in various exercise states. In particular, the specific condition includes the number of heartbeats and the amount of movement obtained when the subject moves at different levels of intensity in a Borg rating of perceived exertion scale (Borg RPE) that ranges from 6 to 20 in the period of time. Optionally, the distance per beat may be tested based on clinical conditions of 6-minute walk test. In particular, the corresponding specific condition is the number of heartbeats and the amount of movement obtained when the subject moves at intensities below level 11 in the Borg rating of perceived exertion scale that ranges from 6 to 20 in the period of time. Optionally, the distance per beat may be data obtained in a running state. In particular, the corresponding specific condition is that the subject moves at intensities above level 12 in the Borg rating of perceived exertion scale that ranges from 6 to 20 in the period of time.

Specifically, the Borg rating of perceived exertion scale that ranges from 6 to 20 is common knowledge in the technical field to which the present invention belongs to estimate exercise or activity intensity. In particular, each level of physical activity perceived by an individual in the Borg rating of perceived exertion scale is associated with heart rate, which is suitable for calculating the energy consumption of heart, and the heart rate is positively correlated with the corresponding level. Table 1 shows the Borg rating of perceived exertion scale that ranges from 6 to 20.

TABLE 1

| Borg rating of perceived exertion scale that ranges from 6 to 20. | |
| --- | --- |
| Level | Intensity of feelings |
| 6 | No exertion |
| 7 | Extremely light |
| 8 | |
| 9 | Very light |
| 10 | |
| 11 | Light |
| 12 | |
| 13 | Somewhat hard |
| 14 | |
| 15 | Hard |
| 16 | |
| 17 | Very hard |
| 18 | |
| 19 | Extremely hard |
| 20 | Maximal exertion |

According to the above contents and the research results and statistical results of the experiments corresponding to the present invention (especially the results that have a p value not greater than 0.05 and have statistical significance), the following relationships between the distance per beat and the cardiac function based on the amount of movement measured in centimeters are obtained. When the distance per beat is less than 35, it indicates that the subject is at high risk of heart failure of class III to IV. When the distance per beat is not less than 35 but less than 40, it indicates that the subject is at high risk of heart failure of class I to II. When the distance per beat is not less than 40 but less than 50, it indicates that the subject is at a first health level, which is equivalent to the cardiac function of an ordinary healthy adult. When the distance per beat is not less than 50 but less than 55, it indicates that the subject is at a second health level, which is equivalent to the cardiac function of an ordinary healthy teenager. When the distance per beat is not less than 55 but less than 60, it indicates that the subject is at a third health level, which is equivalent to highly healthy cardiac function. When the distance per beat is not less than 60 and not greater than 65, it indicates that the subject is at a fourth health level, which is equivalent to highly healthy and trained cardiac function (common in trained and healthy athletes). When the distance per beat is greater than 65 and not less than 70, it indicates that the subject is at high risk of heart failure of class I to II. When the distance per beat is greater than 70, it indicates that the subject is at high risk of heart failure of class III to IV. It should be noted that the distance per beat mentioned in the present invention may be measured in any exercise state, preferably tested under the condition of 6-minute walk test. It is preferred that the 6 minutes of light walking corresponds to levels 6 to 11 in the Borg rating of perceived exertion scale. It should be noted, based on said formula of DPM, for respective measuring devices, respective applying statistical method and respective testing groups (for example, with a specific diagnosis or a specific condition), said values of said intervals for defining said classes I to IV and said first to fourth health level may be different accordingly.

As mentioned above, in terms of health ranking, the fourth health level is better than the third health level, the third health level is better than the second health level, and the second health level is better than the first health level. The extent of heart failure is functionally classified by the NYHA (New York Heart Association). Those classified as class I are asymptomatic in general activities and have no restrictions on any activities. Those classified as class II feel comfortable at rest or light exercise, and have mild restrictions on activities. Those classified as class III feel comfortable only at rest and have restrictions on any activities. Those classified as class IV feel uncomfortable even at rest and feel uncomfortable on any activities. Preferably, corresponding to the application of the distance per beat in the present invention, the subject can clearly understand whether his/her current heart load is in a healthy state (corresponding to the first to fourth health levels) or is at high risk (corresponding to the heart failure classes I to IV).

In particular, according to the research results of relevant experiments of the present invention, the physiological mechanism of the distance per beat is further described as follows. Clinically, the diagnosis of heart failure will be done by measuring blood output per heartbeat by using a Doppler ultrasound and expressing a corresponding functional indicator by an ejection fraction. A lower ejection fraction indicates a less blood output per heartbeat. Therefore, the blood perfused to the extremities (hands and feet) of the body will be reduced, and it can be inferred that the walking speed will decrease correspondingly. However, if a heart failure patient actively wants to increase the walking speed, the heart rate needs to be increased to achieve the blood perfusion required by the body, so that the distance per beat decreases. In addition, in the situation where the distance per beat increases, the number of heartbeats of the subject may decrease (sudden or acute heart failure) due to physiologically or etiologically insufficient energy supplied to the heart to beat, so that the distance per beat increases. Alternatively, due to physiological or etiological limitations, there is an upper limit of heart rate, or heartbeat signals are weak due to weak heart muscle strength (such as old age or illness) and thus are not detected, so that the distance per beat increases. Therefore, a distance per beat on a high side or on a low side may indicate an increased risk of heart failure. In particular, the present invention provides an appropriate assessment indicator between the amount of movement and the heart rate of the subject based on taking a distance as the indicator of the amount of movement of the subject.

For example, if a current hourly speed of the subject is 3 kilometers per hour, and a heart rate is 100 beats per minute, the hourly speed may be converted into a minute speed (5000 centimeters per minute), and the minute speed is divided by the heart rate to obtain a corresponding distance per beat of 50 (centimeters/beat), corresponding to the second health level. In another example, if a current hourly speed of jogging of the subject is 9 kilometers per hour, and a heart rate is 150 beats per minute, a corresponding distance per beat may be calculated to be 100, corresponding to heart failure class III to IV (at high risk). It should be noted that the distance per beat of the present invention may be aimed at all healthy subjects and may especially be aimed at those who have high risk in heart health. In addition, the distance per beat may be adjusted correspondingly for particularly healthy people, people with regular exercise habits, and athletes, for example, by setting a higher permitting range.

With reference to FIG. 2, optionally, according to the research results and statistical results of the experiments corresponding to the present invention, there is also a corresponding step S3 as follows. In the process of calculating the distance per beat, pre-define a first threshold interval and an optional second threshold interval based on an effective statistical confidence interval, and determine a relationship between the distance per beat and the first threshold interval and between the distance per beat and the second threshold interval through the computing unit 3, to generate corresponding signals for the subject or a monitor to know a current heart state of the subject in real time. The heart state may be, for example, classified into: a healthy state, a first warning state, and a second warning state. The first threshold interval includes a first upper limit and a first lower limit, with the first upper limit greater than the first lower limit. The second threshold interval includes a second upper limit and a second lower limit, with the second upper limit greater than the second lower limit, the second upper limit greater than the first upper limit, and the second lower limit less than the first lower limit. In practice, machine learning techniques (such as the so-called AI or deep learning) can be applied by inputting data from confirmed diagnostic cases for a specific symptom or condition into a learning model (such as the so-called neural network) to generate at least one threshold value or range for determining the specific symptom or condition.

For example, when the amount of movement is measured in centimeters, the healthy state means that the distance per beat does not exceed the first threshold interval; the first warning state means that the distance per beat exceeds the first threshold interval (that is, greater than the first upper limit or less than the first lower limit) but does not exceed the second threshold interval; and the second warning state means that the distance per beat exceeds the second threshold interval (that is, greater than the second upper limit or less than the second lower limit). Preferably, the first upper limit is 65, the first lower limit is 40, the second upper limit is 70, and the second lower limit is 35. In other words, when the measured value (the distance per beat) is within the first threshold interval (for example, 40 to 65), the corresponding subject has healthy cardiac function; when the measured value is within the first threshold interval and the second threshold interval, the corresponding subject should pay attention to the current heart condition, and it is recommended to ease the current activity; and when the measured value exceeds the second threshold interval, the corresponding subject should pay close attention to the current heart condition, and it is recommended to stop the current activity immediately. In particular, the above threshold intervals are defined in the process of testing based on the condition of 6-minute walk test.

Optionally, the computing unit 3 may be coupled to a display device and a speaker, to present a current state of cardiac function of a subject to the subject or a monitor. The display device may be, for example, a screen of a smart watch worn on the subject or a display (screen) of any one of a mobile phone, a tablet computer, and a computer, and preferably may display lights or patterns of different colors and achieve conspicuous and visual warning by distinguishing states through the colors. For example, when the heart of the subject is in a healthy state, the corresponding display device may display text representing "healthy/normal", emit a green light, display a green pattern, and the like. When the heart of the subject is in a first warning state, the corresponding display device may display text representing "pay attention", emit a yellow or orange light, display a yellow or orange pattern, and the like, and may be configured with a speaker to emit a sound representing "pay attention". When the heart of the subject is in a second warning state, the corresponding display device may display text representing "please take a rest immediately", emit a red light, display a red pattern, and the like, and may be configured with a speaker to emit a sound representing "please take a rest immediately". Optionally, for those who have experienced heart failure, those who are at high risk of heart failure, those who need to monitor cardiac function in a short term (for example, those who have just had heart-related surgery), or those who have requested, the computing unit 3 may send an instant message/signal to a preset monitoring unit, so as to care about the health condition of the subject in real time and avoid the danger of the subject. The instant message includes sending a short message, sending an automatic report message, and sending a request for an ambulance resource message. These messages optionally include identity information of the subject, a current distance per beat, other physiological information (heartbeat, blood pressure, blood oxygen, etc.), a current location, and the like. The monitoring unit is a clinic, a hospital, a police station, an ambulance station, or preset monitoring personnel who assist and care for the subjects. In addition, the above information in various states may be presented to a monitor (such as medical personnel or a coach) who assists the subject in rehabilitation or exercise, so that the monitor can adjust the exercise intensity at any time.

Alternatively, in addition to using the distance per beat, the first threshold, and the second threshold as the bases for determining, a normalized three-kilometer distance per beat (CMPB3) is also defined (corresponding to the step S2) by multiplying the distance per beat by 3 and dividing the product by the speed (obtained by dividing the amount of movement by the period of time, and converted to a unit of km/hr) of the subject in the period of time, and a preset standard value is used as the reference. As the difference between the normalized three-kilometer distance per beat and the preset standard value is closer, the state of an estimated person is more normal/neutral (i.e., indicating a lower risk of heart failure). Conversely, as the difference between the normalized three-kilometer distance per beat and the preset standard value is higher, the state of an estimated-person is more abnormal (i.e. indicating a higher risk of heart failure).

Specifically, the normalized three-kilometer distance per beat can be referred to in Studenski et al., 2011. The literature pointed out that if the walking speed after age and sex corrections is greater than about 0.8 m/s (about 2.88 km/h), the life expectancy is greater than the median.

Preferably, when the amount of movement is measured in centimeters, the preset standard value corresponding to the normalized three-kilometer distance per beat may be 45 to 55. This range may be divided into ten equal unit intervals based on the least significant digit as an adjustment value, that is, the preset standard value may be adjusted to 45.0, 45.1, 45.2, . . . , 54.9, or 55.0 by a step of 0.1. Preferably, the preset standard value is 50. Alternatively, when the amount of movement is measured in meters, the corresponding preset standard value may be preferably 0.45 to 0.55. This range may be divided into ten equal unit intervals based on the least significant digit as an adjustment value. Preferably, the preset standard value is 0.5.

Preferably, based on the normalized three-kilometer distance per beat and the preset standard value, a tolerance/threshold (valve value) may be set, and a judgment may be made depending on whether an absolute value of a difference between the normalized three-kilometer distance per beat (a measured value for a subject) and the preset standard value is greater than the tolerance (especially done by the computing unit 3, corresponding to the step S3 in FIG. 2). When the difference between the normalized three-kilometer distance per beat (the measured value) and the preset standard value is greater than the tolerance, the computing unit 3 generates/sends a warning signal to warn the subject to pay attention to the current exercise intensity and/or physical condition. It should be noted that the tolerance may have different values for different people. When the amount of movement is measured in centimeters, preferably, the tolerance may be set to 5 to 30 and may be adjusted to 5.0, 5.1, 5.2, . . . , 29.9, or 30.0 by a step of 0.1. Preferably, the tolerance may be set to 20. In particular, for example, in the condition that the difference does not exceed one tolerance (for example, the measured value falls within the range defined by the preset standard value 50±one tolerance 10) may be the healthy state; in the condition that the difference exceeds one tolerance may be the first warning state; and in the condition that the difference exceeds two tolerances (for example, the measured value exceeds the range defined by the preset standard value 50±two tolerances 20) may be the second warning state.

It shall be noted that, based on our research, it has been found that the DPB (Distance Per Beat) can be applied as a useful, reliable and indicative reference value/indicator for evaluating persons with different heathy status. In practical applications, the DPB can be applied to evaluate persons in normal health or in any one of heart failures class I-III. For a person with a normal health condition, the preset standard value of the DPB, measured in centimeters per beat, can be defined as "50". Specifically, this preset standard value is calculated and determined based on an expected condition for the normal health person with average speed at 3 km/h and heart rate at 100 beats per minute in a running test. For a person belonging class I of heart failure, a modified standard value of the DPB, measured in centimeters per beat, may be defined as "40" or may be defined about 80 percent of the preset standard value. Specifically, this modified standard value is calculated based on an expected condition for the heart failure class I person with average speed at 2 km/h and heart rate at 80 beats per minute in a running test. For a person belonging class II of heart failure, a modified standard value of the DPB, measured in centimeters per beat, may be defined as "33.4" or may be defined about 70 percent of the preset standard value. Specifically, this modified standard value is calculated based on an expected condition for the heart failure class II person with average speed at 1.5 km/h and heart rate at 70 beats per minute in a running test. For a person belonging class III of heart failure, a modified standard value of the DPB, measured in centimeters per beat, may be defined as "23.8" or may be defined about 50 percent of the preset standard value. Specifically, this modified standard value is calculated based on an expected condition for the heart failure class III person with average speed at 1 km/h and heart rate at 70 beats per minute in a running test. Additionally, for a person having normal health but confronting a special condition, such as insufficient sleep, a modified standard value of the DPB, measured in centimeters per beat, may be defined as "28" or maybe defined about 60 percent of the preset standard value. Specifically, this modified standard value is calculated based on an expected condition for the insufficient-sleep normal health person with average speed at 2 km/h and heart rate at 120 beats per minute in a running test. Optionally, the corresponding tolerance for the preset or modified standard value in each condition can be set as 10% to 20% of the preset or modified standard value. Preferably, when the difference between the DPB (measured from a user) and the preset or modified standard value is greater than the corresponding tolerance, the warning signal is generated to warn the user.

In addition, according to the research results and statistical results of the experiments corresponding to the present invention, as shown in Table 2 and Table 3, the distance per beat is positively correlated with each of a maximum oxygen consumption ($VO_2$ Max), an anaerobic threshold (AT), an oxygen pulse ($O_2$ pulse), a cardio force index with peak acceleration (CFI_PA) of the subject. The indicators may be used as references for different aspects of cardiac function.

Table 2 shows a relationship between the distance per beat (corresponding to CMPB in Table 1) and the cardio force index with peak acceleration (corresponding to CFI_PA in Table 1) when the amount of movement is measured in centimeters according to the research results of the present invention. Based on a difference between pre-test and post-test, at the 1st minute after the start, a ratio of an average value of the distance per beat (CMPB) to an average value of the cardio force index with peak acceleration (CFI_PA) is about 6:1 (in this case, the average value of the difference of CMPB is 5.277, and the average value of the difference of CFI_PA is 0.879); at the 2nd minute after the start, a ratio of an average value of the distance per beat (CMPB) to an average value of the cardio force index with peak acceleration (CFI_PA) is about 6:1 (in this case, the average value of the difference of CMPB is 4.945, and the average value of the difference of CFI_PA is 0.824); and so on. The cardio force index (CFI) is obtained by multiplying a weight of the subject in a period of time by an exercise acceleration and dividing the product by a heart rate, and the cardio force index with peak acceleration (CFI_PA) is a maximum cardio force index calculated in the period of time. For example, in one minute, a cardio force index may be calculated in every second (in other words, 60 cardio force indexes may be calculated in one minute), and a maximum cardio force index may be selected from the cardio force indexes as the cardio force index with peak acceleration. Wherein, in Table 2, the unit of "Heart Rate" is beats per minute (BPM), and the unit of "Speed" is kilometers per hour (km/hr). "CMPB3" represents the normalized three-kilometer distance per beat, and the unit of "CMPB3" is centimeters per beat.

TABLE 2

Relationship between distance per beat and cardiac force
index with peak acceleration.
Difference of cardiac force index parameter before and after
cardiac rehabilitation (n = 7)

| | Pre-test | Post-test | Difference | p-value[a] | p-value[b] |
|---|---|---|---|---|---|
| Heart_Rate_1st minute after start | 88.449 ± 9.113 | 94.927 ± 11.235 | 6.478 ± 8.798 | 0.099 | 0.091 |
| Heart_Rate_ 2nd minute after start | 88.850 ± 8.353 | 95.442 ± 10.852 | 6.591 ± 8.194 | 0.077 | 0.028 |
| Heart_Rate_ 3rd minute after start | 89.121 ± 8.132 | 95.934 ± 11.214 | 6.813 ± 8.789 | 0.086 | 0.043 |
| Heart_Rate_ 4th minute after start | 89.328 ± 8.283 | 96.318 ± 11.232 | 6.990 ± 9.020 | 0.086 | 0.043 |
| Heart_Rate_ 5th minute after start | 89.367 ± 8.157 | 96.421 ± 11.197 | 7.055 ± 9.023 | 0.084 | 0.043 |
| Heart_Rate_ 6th minute after start | 89.286 ± 8.104 | 96.592 ± 11.142 | 7.306 ± 9.073 | 0.077 | 0.028 |
| Speed_ 1st minute after start | 1.662 ± 0.342 | 2.066 ± 0.405 | 0.403 ± 0.471 | 0.064 | 0.063 |
| Speed_ 2nd minute after start | 1.709 ± 0.232 | 2.066 ± 0.420 | 0.357 ± 0.372 | 0.044 | 0.063 |
| Speed_ 3rd minute after start | 1.728 ± 0.208 | 2.069 ± 0.409 | 0.341 ± 0.370 | 0.051 | 0.063 |
| Speed_ 4th minute after start | 1.730 ± 0.203 | 2.081 ± 0.414 | 0.351 ± 0.357 | 0.041 | 0.063 |
| Speed_ 5th minute after start | 1.739 ± 0.215 | 2.076 ± 0.410 | 0.338 ± 0.353 | 0.045 | 0.063 |
| Speed_ 6th minute after start | 1.738 ± 0.214 | 2.071 ± 0.405 | 0.334 ± 0.351 | 0.046 | 0.063 |
| CFI_PA_ 1st minute after start | 5.363 ± 1.236 | 6.243 ± 1.919 | 0.879 ± 1.602 | 0.197 | 0.237 |
| CFI_PA_ 2nd minute after start | 5.351 ± 1.101 | 6.176 ± 1.883 | 0.824 ± 1.351 | 0.158 | 0.176 |
| CFI_PA_ 3rd minute after start | 5.451 ± 0.997 | 6.160 ± 1.882 | 0.709 ± 1.506 | 0.259 | 0.237 |
| CFI_PA_ 4th minute after start | 5.450 ± 1.002 | 6.177 ± 1.906 | 0.726 ± 1.487 | 0.244 | 0.237 |
| CFI_PA_ 5th minute after start | 5.475 ± 1.035 | 6.152 ± 1.886 | 0.677 ± 1.463 | 0.267 | 0.237 |
| CFI_PA_ 6th minute after start | 5.477 ± 1.030 | 6.124 ± 1.860 | 0.648 ± 1.453 | 0.283 | 0.237 |
| CMPB_ 1st minute after start | 32.180 ± 7.418 | 37.457 ± 11.512 | 5.277 ± 9.611 | 0.197 | 0.237 |
| CMPB_ 2nd minute after start | 32.108 ± 6.609 | 37.053 ± 11.295 | 4.945 ± 8.106 | 0.158 | 0.176 |
| CMPB_ 3rd minute after start | 32.703 ± 5.981 | 36.960 ± 11.293 | 4.257 ± 9.038 | 0.259 | 0.237 |
| CMPB_ 4th minute after start | 32.701 ± 6.009 | 37.059 ± 11.436 | 4.358 ± 8.924 | 0.244 | 0.237 |

TABLE 2-continued

Relationship between distance per beat and cardiac force
index with peak acceleration.
Difference of cardiac force index parameter before and after
cardiac rehabilitation (n = 7)

|  | Pre-test | Post-test | Difference | p-value[a] | p-value[b] |
|---|---|---|---|---|---|
| CMPB_<br>5th minute<br>after start | 32.848 ± 6.209 | 36.912 ± 11.317 | 4.064 ± 8.780 | 0.267 | 0.237 |
| CMPB_<br>6th minute<br>after start | 32.859 ± 6.179 | 36.746 ± 11.159 | 3.887 ± 8.716 | 0.283 | 0.237 |
| CMPB3_<br>1st minute<br>after start | 56.803 ± 5.733 | 53.331 ± 11.512 | −3.473 ± 5.031 | 0.118 | 0.091 |
| CMPB3_<br>2nd minute<br>after start | 56.678 ± 5.054 | 52.997 ± 6.078 | −3.681 ± 4.519 | 0.075 | 0.028 |
| CMPB3_<br>3rd minute<br>after start | 56.497 ± 4.865 | 52.767 ± 6.223 | −3.729 ± 4.871 | 0.089 | 0.043 |
| CMPB3_<br>4th minute<br>after start | 56.380 ± 4.911 | 52.555 ± 6.201 | −3.825 ± 4.988 | 0.088 | 0.043 |
| CMPB3_<br>5th minute<br>after start | 56.350 ± 4.835 | 52.491 ± 6.173 | −3.859 ± 4.959 | 0.085 | 0.043 |
| CMPB3_<br>6th minute<br>after start | 56.397 ± 4.819 | 52.389 ± 6.110 | −4.008 ± 4.955 | 0.076 | 0.043 |

The continuous variable is presented as mean ± standard deviation (Mean ± SD).
[a]Paired sample t-test;
[b]Nonparametric test (Wilcoxon signed rank test).

Table 3 shows a relationship between the distance per beat and each of the physiological indexes (a maximum oxygen consumption, an anaerobic threshold/AT, and an oxygen pulse/$O_2$ pulse) when the amount of movement is measured in centimeters according to the research results of the present invention. Based on a difference between pre-test and post-test, at 1 to 6 minutes after the start, a ratio of an average value of the maximum oxygen consumption and an average value of the distance per beat (CMPB) is about 0.5 to 0.7 (in Table 2, at the 1st minute after the start, 2.69 is divided by 5.277, and at the 6th minute after the start, 2.69 is divided by 3.887). In other words, when the distance per beat increases by 1 unit, the maximum oxygen consumption increases by about 0.5-0.7 mL/Kg/min. Based on a difference between pre-test and post-test, at 1 to 6 minutes after the start, a ratio of an average value of the anaerobic threshold (AT) and an average value of the distance per beat (CMPB) is about 0.039 to 0.054 (in Table 2, at the 1st minute after the start, 3.01 is divided by 5.277, and at the 6th minute after the start, 3.01 is divided by 3.887). In other words, when the distance per beat increases by 1 unit, the anaerobic threshold increases by about 0.039-0.054 L/min. Based on a difference between pre-test and post-test, at 1 to 6 minutes after the start, a ratio of an average value of the oxygen pulse ($O_2$ pulse) and an average value of the distance per beat (CMPB) is about 0.20 to 0.27 (in Table 2, at the 1st minute after the start, 1.06 is divided by 5.277, and at the 6th minute after the start, 1.06 is divided by 3.887). In other words, when the distance per beat increases by 1 unit, the oxygen pulse increases by about 0.20-0.27 mL/beat.

TABLE 3

Relationship between distance per beat and each of
physiological indexes.

Difference of cardio force index parameter before and after cardiac
rehabilitation (n = 7)

|  | Pre-test | Post-test | Difference | p-value[a] | p-value[b] |
|---|---|---|---|---|---|
| CMPB_<br>1st minute after<br>start | 32.180 ± 7.418 | 37.457 ± 11.512 | 5.277 ± 9.611 | 0.197 | 0.237 |
| CMPB_<br>2nd minute after<br>start | 32.108 ± 6.609 | 37.053 ± 11.295 | 4.945 ± 8.106 | 0.158 | 0.176 |
| CMPB_<br>3rd minute after<br>start | 32.703 ± 5.981 | 36.960 ± 11.293 | 4.257 ± 9.038 | 0.259 | 0.237 |
| CMPB_<br>4th minute after<br>start | 32.701 ± 6.009 | 37.059 ± 11.436 | 4.358 ± 8.924 | 0.244 | 0.237 |

TABLE 3-continued

Relationship between distance per beat and each of physiological indexes.

| | | | | | |
|---|---|---|---|---|---|
| CMPB_<br>5th minute after<br>start | 32.848 ± 6.209 | 36.912 ± 11.317 | 4.064 ± 8.780 | 0.267 | 0.237 |
| CMPB_<br>6th minute after<br>start | 32.859 ± 6.179 | 36.746 ± 11.159 | 3.887 ± 8.716 | 0.283 | 0.237 |
| CMPB3_<br>1st minute after<br>start | 56.803 ± 5.733 | 53.331 ± 11.512 | −3.473 ± 5.031 | 0.118 | 0.091 |
| CMPB3_<br>2nd minute after<br>start | 56.678 ± 5.054 | 52.997 ± 6.078 | −3.681 ± 4.519 | 0.075 | 0.028 |
| CMPB3_<br>3rd minute after<br>start | 56.497 ± 4.865 | 52.767 ± 6.223 | −3.729 ± 4.871 | 0.089 | 0.043 |
| CMPB3_<br>4th minute after<br>start | 56.380 ± 4.911 | 52.555 ± 6.201 | −3.825 ± 4.988 | 0.088 | 0.043 |
| CMPB3_<br>5th minute after<br>start | 56.350 ± 4.835 | 52.491 ± 6.173 | −3.859 ± 4.959 | 0.085 | 0.043 |
| CMPB3_<br>6th minute after<br>start | 56.397 ± 4.819 | 52.389 ± 6.110 | −4.008 ± 4.955 | 0.076 | 0.043 |

Difference of cardiopulmonary function parameter before and after (n = 7)

| Name of variable | Pre-test | Post-test | Difference | p-value[a] | p-value[b] |
|---|---|---|---|---|---|
| Maximum oxygen<br>consumption<br>(ml/kg/min) | 20.97 ± 4.45 | 23.66 ± 4.48 | 2.69 ± 3.31 | 0.076 | *0.043 |
| Maximum oxygen<br>consumption<br>Percentage (%) | 85.98 ± 24.24 | 96.76 ± 20.71 | 10.77 ± 11.27 | *0.045 | *0.028 |
| Cardiorespiratory<br>endurance<br>(METs) | 5.99 ± 1.27 | 6.76 ± 1.28 | 0.77 ± 0.95 | 0.076 | *0.043 |
| AT (L/min) | 0.71 ± 0.16 | 0.92 ± 0.31 | 0.21 ± 0.22 | *0.046 | 0.063 |
| AT (ml/kg/min) | 10.06 ± 2.27 | 13.07 ± 4.60 | 3.01 ± 3.20 | *0.047 | 0.063 |
| AT % Predicted<br>Max VO2 (%) | 34.00 ± 11.94 | 44.29 ± 20.69 | 10.29 ± 11.66 | 0.058 | 0.063 |
| O2 pulse<br>(ml/beat) | 11.67 ± 1.89 | 12.73 ± 1.26 | 1.06 ± 1.17 | 0.053 | *0.046 |
| O2 pulse<br>Percentage (%) | 85.84 ± 15.96 | 93.82 ± 14.85 | 7.99 ± 9.34 | 0.090 | 0.075 |

AT: Anaerobic Threshold;
O2 pulse: Oxygen Pulse.
The continuous variable is presented as mean ± standard deviation (Mean ± SD).
[a]Paired sample t-test;
[b]Nonparametric test (Wilcoxon signed rank test).

In summary, by the auxiliary assessment method and system for cardiac function of the present invention, the defined distance per beat can be calculated based on the easy-to-measure physical quantities (an amount of movement and a number of heartbeats), which is adapted to assessment of cardiac function. In addition, through the defined specific data collection, the validity and reliability of the defined distance per beat and/or the normalized three-kilometer distance per beat for assessment of cardiac function can be improved. Moreover, whether to send a warning signal can be determined through the defined assessment standard, for a subject to know his/her current condition in real time. Furthermore, the defined distance per beat can be mapped to different indicators for assessment of cardiac function according to a certain relationship, so as to comprehensively and effectively assess the cardiac function through different aspects of indicators. For example: the degree of progress in cardiac rehabilitation such as EECP (Enhanced External Counter pulsation) program could be evaluated by this auxiliary assessment method and system. With the increase of distance per beat, it implies the progression of cardiac function, which may provide an objective scale for assessment.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. An auxiliary assessment method for cardiac function of a subject, comprising:

measuring, via a heart rate detection unit comprising a physiological sensor configured to detect heartbeats, and via a distance detection unit comprising at least one of a global positioning system (GPS), an accelerometer, a gyroscope, or a device applying triangulation-based positioning, a number of heartbeats of the subject and a cumulative amount of movement of the subject in a period of time, wherein the period of time is defined between at least two adjacent heartbeats;

calculating, by a computing unit coupled to the heart rate detection unit and the distance detection unit:

(i) a distance per beat (centimeter per beat, CMPB), measured in centimeters, by dividing the cumulative amount of movement by the number of heartbeats in the period of time;

(ii) a speed of the subject in kilometers per hour by dividing the cumulative amount of movement by the period of time; and (iii) a normalized three-kilometer distance per beat (CMPB3) by multiplying the CMPB by 3 and dividing the product by the speed;

comparing the CMPB3 with a predefined standard value of the CMPB3 from 50, 40, 33.4, or 23.8, based on a health condition of the subject;

automatically generating a warning signal when an absolute difference between the CMPB3 and the predefined standard value exceeds a tolerance ranging from 5 to 30; and transmitting the warning signal to a display device configured to present a visual indication of cardiac function status using lights or patterns of different colors.

2. The auxiliary assessment method for cardiac function as claimed in claim 1, wherein the number of heartbeats and the cumulative amount of movement are measured under a specific condition, and the specific condition includes the number of heartbeats and the cumulative amount of movement obtained when the subject moves at different levels of intensity in a Borg rating of perceived exertion scale that ranges from 6 to 20 in the period of time.

3. The auxiliary assessment method for cardiac function as claimed in claim 1, wherein in the step of calculating the CMPB, a first threshold interval is predefined based on an effective statistical confidence interval, the first threshold interval includes a first upper limit and a first lower limit, and when the CMPB is greater than the first upper limit or less than the first lower limit, a first warning signal is sent.

4. The auxiliary assessment method for cardiac function as claimed in claim 1, wherein for a person belonging class I of heart failure, a the predefined standard value of the CMPB3 is 40, which is 80% of the predefined standard value of the CMPB3 of 50 for a person with normal health condition.

5. The auxiliary assessment method for cardiac function as claimed in claim 4, wherein the tolerance ranges 10% to 20% of the predefined standard value of the CMPB3 of 40, and a warning signal is generated when an absolute value of a difference between CMPB3 and the predefined standard value of the CMPB3 of 40 is greater than a tolerance.

6. The auxiliary assessment method for cardiac function as claimed in claim 1, wherein for a person belonging class II of heart failure, the predefined standard value of the CMPB3 is 33.4.

7. The auxiliary assessment method for cardiac function as claimed in claim 6, wherein the tolerance ranges 10% to 20% of the predefined standard value of the CMPB3 of 33.4, and a warning signal is generated when an absolute value of a difference between the CMPB3 and the predefined standard value of the CMPB3 of 33.4 is greater than the tolerance.

8. The auxiliary assessment method for cardiac function as claimed in claim 1, wherein for a person belonging class III of heart failure, the predefined standard value of the CMPB3 is 23.8.

9. The auxiliary assessment method for cardiac function as claimed in claim 8, wherein the tolerance ranges 10% to 20% of the predefined standard value of the CMPB3 of 23.8, and a warning signal is generated when an absolute value of a difference between the CMPB3 and the predefined standard value of the CMPB3 of 23.8 is greater than the tolerance.

10. The auxiliary assessment method for cardiac function as claimed in claim 1, wherein the CMPB3 is positively correlated with a maximum oxygen consumption of the subject.

11. The auxiliary assessment method for cardiac function as claimed in claim 1, wherein the CMPB3 is positively correlated with an anaerobic threshold of the subject.

12. The auxiliary assessment method for cardiac function as claimed in claim 1, wherein the CMPB3 is positively correlated with an oxygen pulse of the subject.

13. The auxiliary assessment method for cardiac function as claimed in claim 1, wherein the CMPB3 is positively correlated with a cardiac force index with peak acceleration.

14. An auxiliary assessment system for cardiac function, comprising:

a heart rate detection unit comprising a physiological sensor configured to measure a number of heartbeats of a subject in a period of time;

a distance detection unit comprising at least one of a global positioning system (GPS), an accelerometer, a gyroscope, or a device applying triangulation-based positioning, the distance detection unit being configured to measure a cumulative amount of movement of the subject in the period of time, wherein the period of time is defined between at least two adjacent heartbeats;

a computing unit coupled to the heart rate detection unit and the distance detection unit, wherein the computing unit is configured to;

(i) receive the number of heartbeats and the cumulative amount of movement;

(ii) calculate a distance per beat (centimeter per beat, CMPB), measured in centimeters, by dividing the cumulative amount of movement by the number of heartbeats in the period of time;

(iii) calculate a speed of the subject in kilometers per hour by dividing the cumulative amount of movement by the period of time;

(iv) calculate a normalized three-kilometer distance per beat (CMPB3) by multiplying the CMPB by 3 and dividing the product by the speed;

(v) compare the CMPB3 with a predefined standard value of the CMPB3, the predefined standard value of the CMPB3 being selected from 50, 40, 33.4 or 23.8; and (vi) automatically generate a warning signal when an absolute difference between the CMPB3 and the predefined standard value of the CMPB3 exceeds a tolerance ranging from 5 to 30; and a display device coupled to the computing unit and configured to receive the warning signal and present a visual indication of cardiac function using lights or patterns of different colors.

\* \* \* \* \*